United States Patent
Sanwal et al.

(10) Patent No.: US 9,150,542 B2
(45) Date of Patent: Oct. 6, 2015

(54) PROCESS FOR THE PREPARATION OF CRYSTALLINE FORM I OF METHANESULFONATE SALT OF DABIGATRAN ETEXILATE

(71) Applicant: RANBAXY LABORATORIES LIMITED, New Delhi, Delhi (IN)

(72) Inventors: Sudhir Singh Sanwal, Kangra (IN); Anandam Vempali, Nellore (IN); Balaguru Murugesan, Coimbatore (IN); Swargam Sathyanarayana, Gurgaon (IN); Rajesh Kumar Thaper, Jammu (IN); Mohan Prasad, Gurgaon (IN)

(73) Assignee: RANBAXY LABORATORIES LIMITED, New Delhi (IN)

( * ) Notice: Subject to any disclaimer, the term of this patent is extended or adjusted under 35 U.S.C. 154(b) by 0 days.

(21) Appl. No.: 14/420,249

(22) PCT Filed: Sep. 2, 2013

(86) PCT No.: PCT/IB2013/058232
§ 371 (c)(1),
(2) Date: Feb. 6, 2015

(87) PCT Pub. No.: WO2014/033693
PCT Pub. Date: Mar. 6, 2014

(65) Prior Publication Data
US 2015/0197504 A1    Jul. 16, 2015

(30) Foreign Application Priority Data
Aug. 31, 2012 (IN) .......................... 2712/DEL/2012

(51) Int. Cl.
*C07D 401/12* (2006.01)
(52) U.S. Cl.
CPC ..................... *C07D 401/12* (2013.01)
(58) Field of Classification Search
CPC .................................................. C07D 401/12
USPC ..................................................... 546/273.4
See application file for complete search history.

(56) References Cited

U.S. PATENT DOCUMENTS

| 6,087,380 A | 7/2000 | Hauel et al. ............... 514/336 |
| 2005/0234104 A1 | 10/2005 | Schmid et al. ............ 514/338 |

FOREIGN PATENT DOCUMENTS

| CA | 2 609 583 | 12/2006 |
| WO | WO 2006/131491 | 12/2006 |
| WO | WO 2007/071742 | 6/2007 |
| WO | WO 2007/071743 | 6/2007 |
| WO | WO 2008/059029 | 5/2008 |
| WO | WO 2011/110478 | 9/2011 |
| WO | WO 2012/027543 | 3/2012 |
| WO | WO 2012/077136 | 6/2012 |

OTHER PUBLICATIONS

*Preparation of solid forms of Dabigatran etexilate and Dabigatran etexilate mesylate*, published Mar. 14, 2012 on website IP.com as Prior Art Database Disclosure No. I PCOM000215884D.

*Primary Examiner* — Patricia L Morris

(57) ABSTRACT

The present invention relates to a process for the preparation of crystalline Form I of methanesulfonate salt of dabigatran etexilate. (Formula (I)). The present invention does not require the isolation of the dabigatran etexilate intermediate.

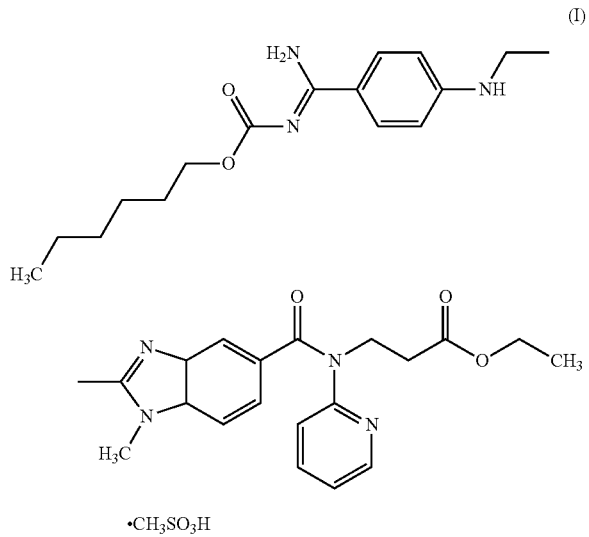

13 Claims, 2 Drawing Sheets

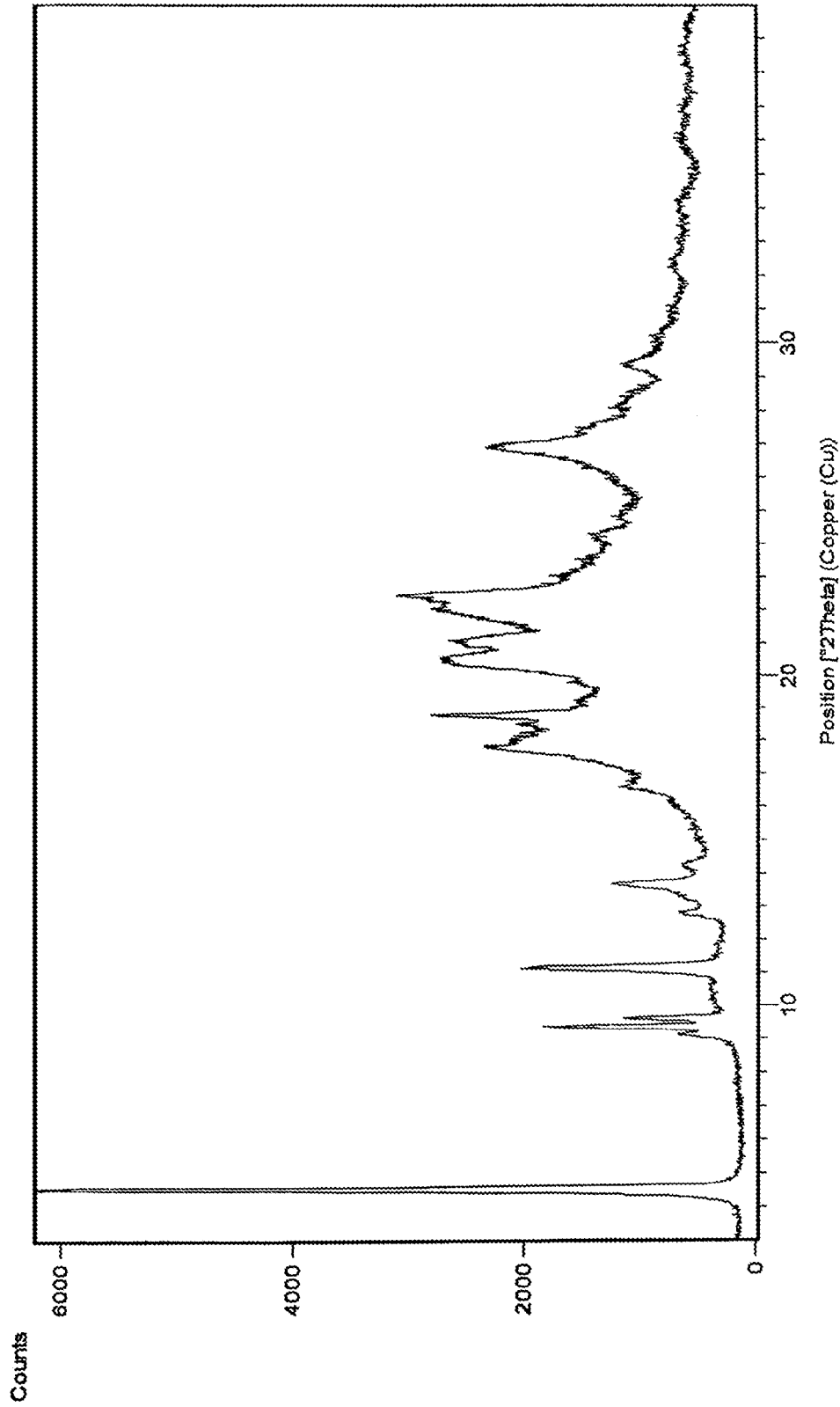
FIGURE 1: X-RAY POWDER DIFFRACTION (XRPD) PATTERN OF CRYSTALLINE FORM 1 OF DABIGATRAN ETEXILATE OBTAINED ACCORDING TO EXAMPLE 1.

FIGURE 1A: TABLE OF VALUES FOR THE XRPD PATTERN DEPICTED IN FIGURE 1.

| Pos. [°2TH.] | d-spacing [Å] | Rel. Int. [%] |
| --- | --- | --- |
| 4.56 | 19.40 | 100 |
| 9.09 | 9.73 | 7.63 |
| 9.38 | 9.43 | 26.54 |
| 9.63 | 9.19 | 15.77 |
| 11.16 | 7.93 | 28.99 |
| 12.80 | 6.92 | 6.11 |
| 13.70 | 6.46 | 14.98 |
| 14.27 | 6.21 | 5.26 |
| 16.58 | 5.35 | 12.84 |
| 17.79 | 4.99 | 32.45 |
| 18.81 | 4.72 | 38.78 |
| 20.41 | 4.35 | 37.51 |
| 21.03 | 4.22 | 35.62 |
| 21.95 | 4.05 | 37.34 |
| 22.45 | 3.96 | 41.68 |
| 24.25 | 3.67 | 13.91 |
| 26.99 | 3.30 | 25.63 |
| 28.33 | 3.15 | 7.61 |
| 29.23 | 3.06 | 6.35 |
| 32.30 | 2.77 | 1.56 |
| 34.09 | 2.63 | 1.75 |
| 36.00 | 2.49 | 1.60 |

PROCESS FOR THE PREPARATION OF CRYSTALLINE FORM I OF METHANESULFONATE SALT OF DABIGATRAN ETEXILATE

FIELD OF THE INVENTION

The present invention relates to a process for the preparation of crystalline Form I of the methanesulfonate salt of dabigatran etexilate. The present invention does not require the isolation of a dabigatran etexilate intermediate.

BACKGROUND OF THE INVENTION

The drug substance used in the commercial drug product formulation of Pradaxa® is the methanesulfonate salt of dabigatran etexilate, which is chemically designated as β-Alanine, N-[[2-[[[4-[[[(hexyloxy)carbonyl]amino]iminomethyl]phenyl]amino]methyl]-1-methyl-1H-benzimidazol-5-yl]carbonyl]-N-2-pyridinyl-, ethyl ester, methanesulfonate salt of Formula I.

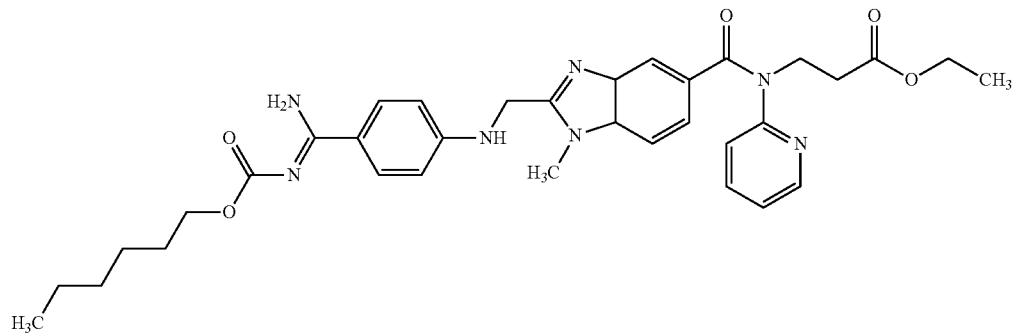

FORMULA I

·CH$_3$SO$_3$H

Dabigatran Etexilate of Formula II

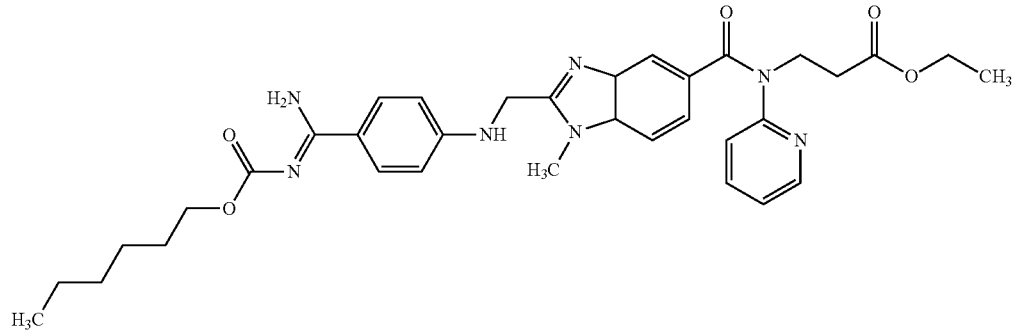

FORMULA II is a prodrug of dabigatran of Formula III

FORMULA III

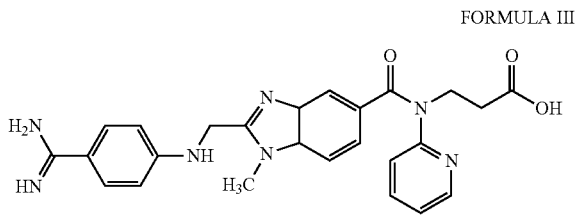 [SMILES: CN1C(CNc2ccc(C(=N)N)cc2)=NC2C=C(C(=O)N(CCC(=O)O)c3ccccn3)C=CC21]

which is a direct thrombin inhibitor. Dabigatran etexilate is indicated to reduce the risk of stroke and systemic embolism in patients with non-valvular atrial fibrillation. It may be used alone or in combination with other therapeutic agents.

U.S. Publication No. 2005/0234104 describes processes for the preparation of crystalline Forms I and II of the methanesulfonate salt of dabigatran etexilate. The crystalline Form I of the methanesulfonate salt of dabigatran etexilate is prepared by dissolving dabigatran etexilate in acetone followed by the addition of a solution of methane sulfonate in acetone.

PCT Publication No. WO 2012/077136 describes a process for the preparation of crystalline Form I of the methanesulfonate salt of dabigatran etexilate using an ester and alcohol solvent system, and specifically using ethyl acetate and ethanol solvents.

Processes for the preparation of dabigatran etexilate and its methanesulfonate salt are also described in U.S. Pat. No. 6,087,380 and PCT Publication Nos. WO 2012/027543, WO 2008/059029, WO 2011/110478, and WO 2006/131491.

SUMMARY OF THE INVENTION

The present inventors have developed a process for the preparation of crystalline Form I of a methanesulfonate salt of dabigatran etexilate. The present process involves the direct addition of a methane sulfonic acid solution to the reaction mixture without isolating a dabigatran etexilate intermediate. The present process is simple and capable of preparing crystalline Form I of a methanesulfonate salt of dabigatran etexilate in a reproducible manner on an industrial scale.

BRIEF DESCRIPTION OF THE DRAWINGS

FIG. 1 depicts the X-ray powder diffraction (XRPD) pattern of crystalline Form I of the methanesulfonate salt of dabigatran etexilate.

FIG. 1A: Table of values for the XRPD pattern depicted in FIG. 1.

DETAILED DESCRIPTION OF THE INVENTION

An aspect of the present invention provides a process for the preparation of crystalline Form I of a methanesulfonate salt of dabigatran etexilate, wherein the process comprises a) contacting ethyl N-[(2-{[(4-carbamimidoylphenyl)amino]methyl}-1-methyl-3a,7a-dihydro-1H-benzimidazol-5-yl)carbonyl]-N-pyridin-2-yl-β-alaninate of Formula IV

FORMULA IV

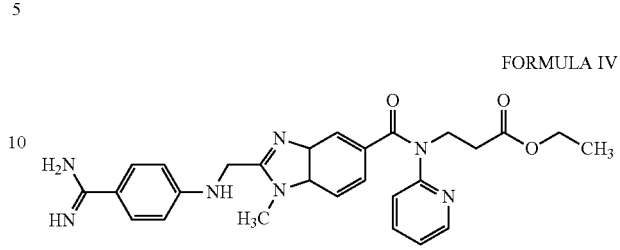

or its salt with n-hexyl chloroformate;
b) treating the reaction mixture obtained in step a) with methane sulfonic acid; and
c) isolating crystalline Form I of the methanesulfonate salt of dabigatran etexilate from the mixture thereof.

The ethyl N-[(2-{[(4-carbamimidoylphenyl)amino]methyl}-1-methyl-3a,7a-dihydro-1H-benzimidazol-5-yl)carbonyl]-N-pyridin-2-yl-β-alaninate of Formula IV or its salt may be prepared according to methods described in the literature, for example, U.S. Pat. No. 6,087,380.

The salts of ethyl N-[(2-{[(4-carbamimidoylphenyl)amino]methyl}-1-methyl-3a,7a-dihydro-1H-benzimidazol-5-yl)carbonyl]-N-pyridin-2-yl-β-alaninate of Formula IV may be selected from hydrochloride, hydrobromide, or acetate salt. The salt of compound of Formula IV is preferably the acetate salt.

The compound of Formula IV is contacted with n-hexyl chloroformate in the presence of a solvent selected from the group consisting of water, ethers, halogenated hydrocarbons, esters, or mixtures thereof. The ether solvent may be selected from the group comprising tetrahydrofuran, diisopropyl ether, or methyl t-butyl ether. The halogenated hydrocarbon solvent may be dichloromethane. The ester solvent may be, for example, ethyl acetate. The solvent is preferably tetrahydrofuran, either alone or in combination with water. Hexyl chloroformate may be used either as a solid or in solution form with tetrahydrofuran.

The compound of Formula IV is contacted with n-hexyl chloroformate in the presence of an organic or inorganic base. The organic base may be selected from the group comprising ethylamine or diisopropyl ethyl amine. The inorganic base may be selected from the group comprising sodium carbonate or potassium carbonate. Preferably, the base is potassium carbonate.

The compound of Formula IV is contacted with n-hexyl chloroformate at a temperature of about 10° C. to about 40° C., for example, about 15° C. to about 25° C. The compound of Formula IV is contacted with n-hexyl chloroformate for about 3 hours to about 6 hours, for example, about 4 hours to about 6 hours.

The reaction mixture may be subjected to carbon treatment. The reaction mixture may optionally be treated with butylated hydroxytoluene. The solvent may be recovered from the reaction mixture and the reaction mixture used as such for the next step.

The present invention does not require the isolation of the dabigatran etexilate intermediate in step a). The reaction mixture obtained in step a) may be treated with methane sulfonic acid in the presence of a solvent selected from the group comprising of ketones, esters, alcohols, or mixtures thereof. The ketone solvent selected from the group comprising acetone, methyl butyl ketone, or methyl isopropyl ketone.

The ester solvent may be selected from the group comprising ethyl acetate, isopropyl acetate, or butyl acetate. The alcohol solvent may be selected from the group comprising ethanol, methanol, n-propanol, or butanol. Preferably, the solvent is acetone. The methane sulfonic acid may be used as a solid or as a solution with acetone.

The reaction mixture obtained in step a) is treated with methane sulfonic acid at a temperature of about 10° C. to about 40° C., for example, about 15° C. to about 25° C. The reaction mixture obtained in step a) is treated with methane sulfonic acid for about 3 hours to about 6 hours, for example, about 4 hours to about 6 hours.

The crystalline Form I of methanesulfonate salt of dabigatran etexilate may be isolated from the reaction mixture by filtration, decantation, evaporation, distillation, or combinations thereof. The crystalline Form I of methanesulfonate salt of dabigatran etexilate has substantially the same XRPD pattern as depicted in FIG. 1, and can further be characterized by differential scanning calorimetry (DSC).

The XRPD of the sample was determined using a Panalytical X'Pert Pro X-Ray Powder Diffractometer in the range 3-40 degree 2 theta and under tube voltage and current of 45 Kv and 40 mA respectively. Copper radiation of wavelength 1.54 angstrom and Xceletor detector was used.

While the present invention has been described in terms of its specific embodiments, certain modifications and equivalents will be apparent to those skilled in the art and are intended to be included within the scope of the present invention.

EXAMPLE

Preparation of Crystalline Form I of Methane Sulfonate Salt of Dabigatran Etexilate The acetate salt of ethyl N-[(2-{[(4-carbamimidoylphenyl) amino]methyl}-1-methyl-3a,7a-dihydro-1H-benzimidazol-5-yl)carbonyl]-N-pyridin-2-yl-β-alaninate (50 g) was added to tetrahydrofuran (750 mL) and deionized water (250 mL) and the mixture was stirred for 20 minutes. Potassium carbonate (37.08 g) was added to the reaction mixture and the mixture was stirred for 30 minutes. A solution of n-hexyl chloroformate (16.19 g) in tetrahydrofuran (250 mL) was added to the reaction mixture at 18° C. to 20° C. The reaction mixture was stirred for 2 hours at 20° C. to 22° C. The reaction mixture was taken in a separating funnel and the tetrahydrofuran layer was collected. Potassium carbonate (40 g) was added to the reaction mixture and the mixture was stirred for 30 minutes.

The layers obtained were separated and the tetrahydrofuran layer was taken. Carbon (5 g) was added to the tetrahydrofuran layer and it was stirred for 20 minutes. The reaction mixture was filtered through celite. The tetrahydrofuran layer was collected and butylated hydroxytoluene (0.5 g) was added to the reaction mixture. The solvents were recovered under vacuum. Acetone (150 mL) was added to the reaction mixture and the mixture was stirred for 20 minutes. The acetone (130 mL) was recovered under vacuum. The solid obtained was dissolved in acetone (392 mL). A solution of methane sulfonic acid (8.14 g) in acetone (56 mL) was added to the reaction mixture at 18° C. to 20° C. The reaction mixture was stirred at 20° C. to 22° C. for 2 hours, filtered, and dried under suction. The reaction mixture was further dried under vacuum at 55° C. for 15 hours to get the title compound having an XRPD pattern as depicted in FIG. 1.

Yield: 52 g
Percentage Yield: 80.6%

We claim:

1. A process for the preparation of crystalline Form I of a methanesulfonate salt of dabigatran etexilate, wherein the process comprises
   a) contacting ethyl N-[(2-{[(4-carbamimidoylphenyl) amino]methyl}-1-methyl-3a,7a-dihydro-1H-benzimidazol-5-yl)carbonyl]-N-pyridin-2-yl-β-alaninate of Formula IV

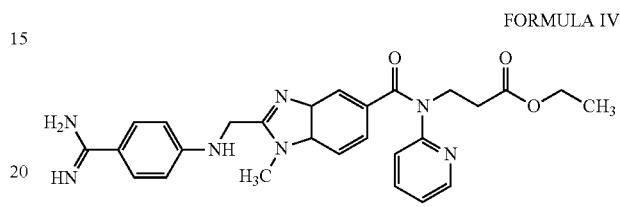

FORMULA IV or salts thereof with n-hexyl chloroformate;
   b) treating the reaction mixture obtained in step a) with methane sulfonic acid; and
   c) isolating the crystalline Form I of the methanesulfonate salt of dabigatran etexilate from the mixture thereof.

2. The process according to claim 1, wherein the salt of the compound Formula IV is selected from hydrochloride, hydrobromide, or acetate salts.

3. The process according to claim 2, wherein the salt of the compound of Formula IV is an acetate salt.

4. The process according to claim 1, wherein the compound of Formula IV is contacted with n-hexyl chloroformate in the presence of a solvent selected from the group consisting of water, ethers, halogenated hydrocarbons, esters, or mixtures thereof.

5. The process according to claim 4, wherein the solvent is tetrahydrofuran, or tetrahydrofuran in combination with water.

6. The process according to claim 1, wherein n-hexyl chloroformate is used either as a solid or in a solution with tetrahydrofuran.

7. The process according to claim 1, wherein the compound of Formula IV is contacted with n-hexyl chloroformate in the presence of a base.

8. The process according to claim 7, wherein the base is potassium carbonate.

9. The process according to claim 1, wherein the product prepared in step a) is not isolated.

10. The process according to claim 1, wherein the reaction mixture obtained in step a) is treated with methane sulfonic acid in a solvent selected from the group consisting of ketones, esters, alcohols, or mixtures thereof.

11. The process according to claim 10, wherein the solvent is acetone.

12. The process according to claim 1, wherein methane sulfonic acid is used as a solid or in solution with acetone.

13. The process according to claim 1, wherein the crystalline Form I of the methanesulfonate salt of dabigatran etexilate has substantially the same XRPD pattern as depicted in FIG. 1.

* * * * *